US008221698B2

(12) United States Patent

Aoki et al.

(10) Patent No.: US 8,221,698 B2
(45) Date of Patent: Jul. 17, 2012

(54) LIQUID CONTAINER

(75) Inventors: Yuji Aoki, Matsumoto (JP); Hitotoshi Kimura, Matsumoto (JP)

(73) Assignee: Seiko Epson Corporation, Tokyo (JP)

( * ) Notice: Subject to any disclaimer, the term of this patent is extended or adjusted under 35 U.S.C. 154(b) by 903 days.

(21) Appl. No.: 11/785,490

(22) Filed: Apr. 18, 2007

(65) Prior Publication Data

US 2007/0243104 A1 Oct. 18, 2007

(30) Foreign Application Priority Data

Apr. 18, 2006 (JP) ............................... P2006-114847
Apr. 16, 2007 (JP) ............................... P2007-107476

(51) Int. Cl.
*G01N 31/22* (2006.01)
*G01N 33/52* (2006.01)
*G01N 35/00* (2006.01)
*B41J 2/175* (2006.01)

(52) U.S. Cl. .......................................... 422/403; 347/86

(58) Field of Classification Search ..................... 422/58
See application file for complete search history.

(56) References Cited

U.S. PATENT DOCUMENTS 6,151,039 A 11/2000 Hmelar et al.
6,435,638 B1 8/2002 Wilson et al.
7,404,628 B2 * 7/2008 Naka et al. ...................... 347/86
2004/0130583 A1 7/2004 Seino et al.
2004/0252146 A1 * 12/2004 Naka et al. ........................ 347/6
2007/0109368 A1 * 5/2007 Kimura ........................... 347/86

FOREIGN PATENT DOCUMENTS

EP 1462263 A2 * 9/2004
JP 2004-136670 A 5/2004

* cited by examiner

*Primary Examiner* — Sam P Siefke
*Assistant Examiner* — Bryan Kilpratick
(74) *Attorney, Agent, or Firm* — Sughrue Mion, PLLC

(57) ABSTRACT

A liquid container includes: a liquid containing chamber that is accommodated in a pressure space and is pressurized by a pressurized fluid to be introduced into the pressure space so as to discharge a liquid stored in an inside thereof; and a liquid detection portion for detecting the liquid in the liquid containing chamber, the liquid detection portion includes: a liquid detection chamber that has a liquid inlet port communicating with the liquid containing chamber and a liquid outlet port communicating with an external liquid consuming apparatus, and a volume of which changes according to a liquid pressure between the liquid inlet port and the liquid outlet port; a detection unit that is provided on one of first and second walls opposite to each other, a distance between the first and second walls changing in accordance with the change in volume of the liquid detection chamber, for detecting a vibration wave form of the liquid; and a space forming portion that, when the volume of the liquid detection chamber is minimized, forms a predetermined space between the first and second walls.

12 Claims, 7 Drawing Sheets

LIQUID CONTAINER

BACKGROUND

1. Technical Field

The present invention relates to a liquid container that supplies a predetermined liquid to a liquid consuming apparatus, for example, a liquid ejection head ejecting a liquid droplet.

2. Related Art

A liquid ejection head of a textile printing apparatus, a micro dispenser, or a commercial recording apparatus that requires ultrahigh printing quality receives a liquid ejected from a liquid container. However, if the liquid ejection head operates in a state where the liquid is not supplied, so-called idle printing occurs, and thus the liquid ejection head is likely to be damaged. In order to prevent this problem, it is necessary to monitor a liquid residual quantity in the container.

As the recording apparatus, there are suggested various apparatuses that have a liquid detection portion for detecting an ink in an ink cartridge as a liquid container.

The specific structure of such a liquid detection portion is described in Patent Document 1. In such a liquid detection portion, a liquid containing concave portion is formed at one of opposing flat surfaces of a flexible pouch containing the liquid, and a piezoelectric vibrator is disposed at outer surface of the concave portion. In addition, a rigid body is disposed at the other surface. Accordingly, an ink residual quantity is detected from a vibration state by a liquid amount (a depth of the liquid) between the rigid body and the piezoelectric vibrator.

Patent Document 1: JP-A-2004-136670

However, in the liquid detection portion described in Patent Document 1, the liquid residual quantity can be detected with relatively high accuracy, but the residual quantity of ink contained in the flexible pouch is affected by bending or wrinkle of the pouch since the rigid body moves according to the deformation of the flexible pouch. Accordingly, detection accuracy may be degraded.

SUMMARY

An advantage of some aspects of the invention is to provide a liquid container that has a liquid detection portion for stably detecting a liquid with high accuracy while preventing bending or wrinkle of a flexible pouch containing a liquid from affecting detection accuracy of the liquid residual quantity. The advantage can be attained by at least one of the following aspects:

(1) A first aspect of the invention provides a liquid container comprising: a liquid containing chamber that is accommodated in a pressure space and is pressurized by a pressurized fluid to be introduced into the pressure space so as to discharge a liquid stored in an inside thereof; and a liquid detection portion for detecting the liquid in the liquid containing chamber. The liquid detection portion includes: a liquid detection chamber that has a liquid inlet port communicating with the liquid containing chamber and a liquid outlet port communicating with an external liquid consuming apparatus, and a volume of which changes according to a liquid pressure between the liquid inlet port and the liquid outlet port; a detection unit that is provided on one of a pair of opposing walls, a distance between the opposing walls changing in accordance with the change in volume of the liquid detection chamber, for detecting a vibration waveform of the liquid; and a space forming portion that, when the volume of the liquid detection chamber is minimized, forms a predetermined space between the opposing walls.

With this configuration, if the liquid residual quantity in the liquid containing chamber decreases, the amount of the liquid to be discharged to the liquid detection chamber decreases, and then the volume of the liquid detection chamber decreases. Accordingly, the detection unit detects the vibration waveform to be applied to the liquid detection chamber on the basis of the decrease in volume of the liquid detection chamber.

Further, the liquid detection chamber is separated from the liquid containing chamber. Accordingly, when the liquid containing chamber contains the liquid in a flexible pouch, even if bending or wrinkle occurs in the flexible pouch due to the decrease in the liquid residual quantity of the liquid containing chamber, bending or wrinkle of the pouch does not affect the detection accuracy of the detection unit.

In addition, even if the liquid in the liquid containing chamber is exhausted and the volume of the liquid detection chamber is minimized, a predetermined space is secured between the detection unit and the opposing wall, such that the vibration waveform can be detected. Therefore, it is possible to detect that the liquid is exhausted.

(2) In the liquid container according to (1) of the invention, the space forming portion may be a protrusion that protrudes from one of the opposing walls.

With this configuration, when a part constituting the pair of opposing walls of the liquid detection chamber is an injection molded product formed of resin, the protrusion can be integrally formed at the surface of the opposing wall, such that the number of parts is not increased. That is, manufacturing costs can be prevented from being increased due to the increase in the number of parts.

(3) In the liquid container according to (2) of the invention, preferably, one wall of the pair of opposing walls of the liquid detection chamber is formed by a diaphragm, and the other wall is formed by a rigid wall, the detection unit is provided at the rigid wall, a pressure receiving plate is provided at the diaphragm to be opposed to the detection unit, and a protrusion serving as the space forming portion is provided at the pressure receiving plate, and a pressure adjusting spring is provided to urge the diaphragm such that the diaphragm is displaced according to the liquid pressure.

With this configuration, if the detection unit is disposed in the liquid detection chamber that is separated from the liquid containing chamber, the liquid detection portion that uses the vibration waveform to be applied to the liquid detection chamber for detecting the liquid can be relatively simply constructed.

(4) In the liquid container according to (2) of the invention, preferably, one wall of the pair of opposing walls of the liquid detection chamber is formed by a diaphragm, and the other wall is formed by a inner wall of the liquid detection chamber, the detection unit is provided at a rigid wall forming a part of the inner wall, a pressure receiving plate is provided at the diaphragm to be opposed to the detection unit, and a protrusion serving as the space forming portion is provided at the inner wall, and a pressure adjusting spring is provided to urge the diaphragm such that the diaphragm is displaced according to the liquid pressure.

With this configuration, similar to (3) of the invention, if the detection unit is disposed in the liquid detection chamber that is separated from the liquid containing chamber, the liquid detection portion that uses the vibration waveform to be applied to the liquid detection chamber for detecting the liquid can be relatively simply constructed.

(5) In the liquid container according to (1) of the invention, preferably, one wall of the pair of opposing walls of the liquid detection chamber is formed by a diaphragm, and the other wall is formed by a inner wall of the liquid detection chamber, the detection unit is provided at a rigid wall forming a part of the inner wall, a pressure receiving plate is provided at the diaphragm to be opposed to the detection unit, and a recess serving as the space forming portion is provided at the pressure receiving plate, and a pressure adjusting spring is provided to urge the diaphragm such that the diaphragm is displaced according to the liquid pressure.

With this configuration, similar to (3) of the invention, if the detection unit is disposed in the liquid detection chamber that is separated from the liquid containing chamber, the liquid detection portion that detects the liquid residual quantity on the basis of the change in the vibration waveform to be applied to the liquid detection chamber can be relatively simply constructed.

(6) In the liquid container according to (2) of the invention, one wall of the pair of opposing walls of the liquid detection chamber is formed by a diaphragm, and the other wall is formed by a inner wall of the liquid detection chamber, the detection unit is provided at the diaphragm and a protrusion serving as the space forming portion is provided at the inner wall, and a pressure adjusting spring is provided to urge the diaphragm such that the diaphragm is displaced according to the liquid pressure.

With this configuration, similar to (3) of the invention, if the detection unit is disposed in the liquid detection chamber that is separated from the liquid containing chamber, the liquid detection portion that uses the vibration waveform to be applied to the liquid detection chamber for detecting the liquid can be relatively simply constructed.

(7) In the liquid container according to (2) of the invention, preferably, one wall of the pair of opposing walls of the liquid detection chamber is formed by a diaphragm, and the other wall is formed by a inner wall of the liquid detection chamber, the detection unit is provided at the diaphragm, and a recess serving as the space forming portion is provided at the inner wall, and a pressure adjusting spring is provided to urge the diaphragm such that the diaphragm is displaced according to the liquid pressure.

With this configuration, similar to (3) of the invention, if the detection unit is disposed in the liquid detection chamber that is separated from the liquid containing chamber, the liquid detection portion that uses the vibration waveform to be applied to the liquid detection chamber for detecting the liquid can be relatively simply constructed.

(8) In the liquid container according to any one of (3) to (7) of the invention, the diaphragm may be formed of a flexible film.

With this configuration, if an aluminum-laminated multilayer film, in which an aluminum layer is laminated on a resin film layer, is used as the flexible film, a high gas barrier property can be secured in the liquid detection chamber. Further, since a degree of deaeration of the liquid contained in the liquid containing chamber is not lowered due to the gas barrier property in the liquid detection chamber, the liquid at a high degree of deaeration can be supplied to the liquid consuming apparatus.

(9) In the liquid container according to (1) to (8) of the invention, the liquid stored in the liquid containing chamber may be ink, and the liquid container may be used for an ink container that supplies ink to an ink jet recording apparatus.

With this configuration, the ink residual quantity in the ink container that supplies ink to the ink jet recording apparatus can be accurately detected. Accordingly, a trouble can be prevented from occurring due to degradation of the detection accuracy or erroneous detection of the ink residual quantity. Therefore, operation reliability in the ink jet recording apparatus can be improved.

In the liquid container according to the aspects of the invention, the change in volume of the liquid detection chamber due to the decrease in the liquid residual quantity of the liquid containing chamber is viewed as the change in the vibration waveform applied to the liquid detection chamber. The vibration waveform is used for detecting the liquid residual quantity in the liquid containing chamber. Further, the liquid detection chamber is separated from the liquid containing chamber. Accordingly, when the liquid containing chamber contains the liquid in the flexible pouch, even if bending or wrinkle occurs in the flexible pouch due to the decrease in the liquid residual quantity of the liquid containing chamber, bending or wrinkle of the pouch does not affect the detection accuracy of the detection unit.

In addition, even if the liquid in the liquid containing chamber is exhausted and the volume of the liquid detection chamber is minimized, a predetermined space is secured between the detection unit and the opposing wall in the liquid detection chamber. Accordingly, if the detection unit is normally operating, the vibration waveform corresponding to the amount of the liquid remaining in the space is detected. Therefore, there is no case where the change in the vibration waveform cannot be detected due to a failure of the detection unit or the like or it is erroneously detected that the liquid is exhausted. As a result, it is possible to accurately detect that the liquid is exhausted.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, preferred embodiments of a liquid container according to the invention will be described in detail with reference to the drawings.

Figure 1:
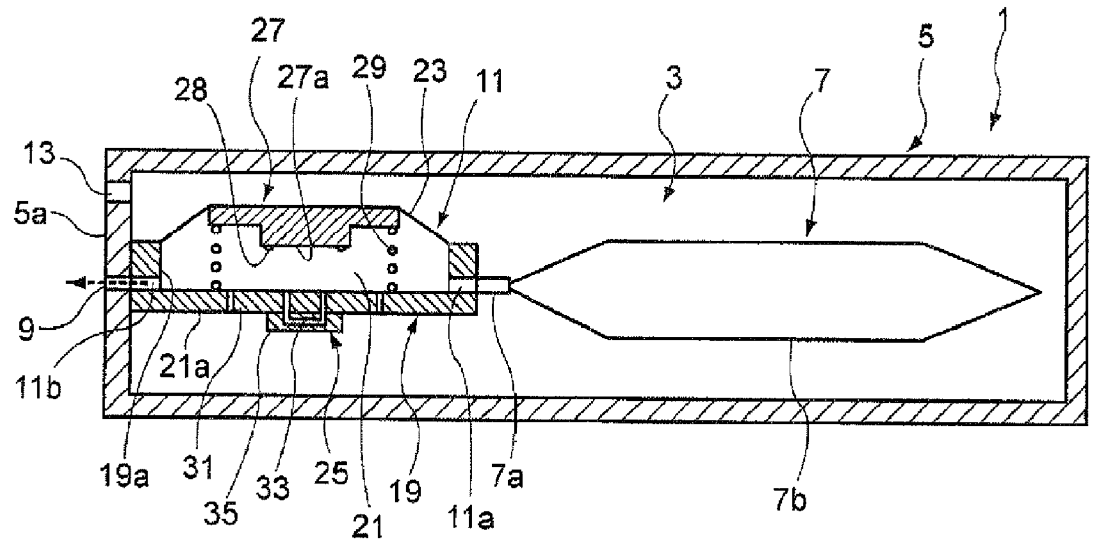
FIG. 1 is a longitudinal cross-sectional view showing a liquid container according to a first embodiment of the invention in a state where a liquid remains in a liquid containing chamber and a pressure space is not pressurized.
Figure 2:
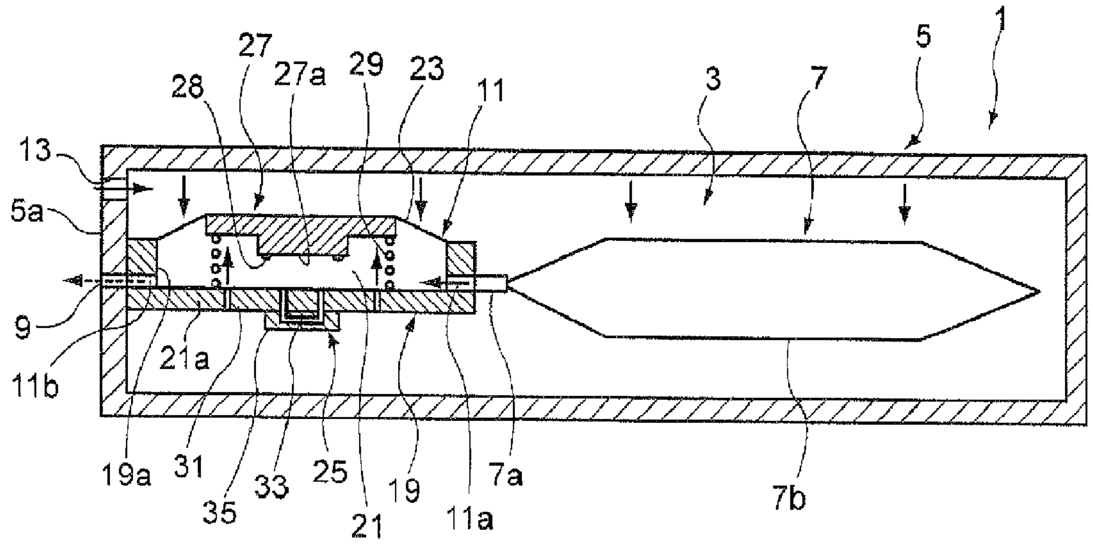
FIG. 2 is a longitudinal cross-sectional view showing a state where a liquid remains in a liquid containing chamber and a pressure space is pressurized in the first embodiment.
Figure 3:
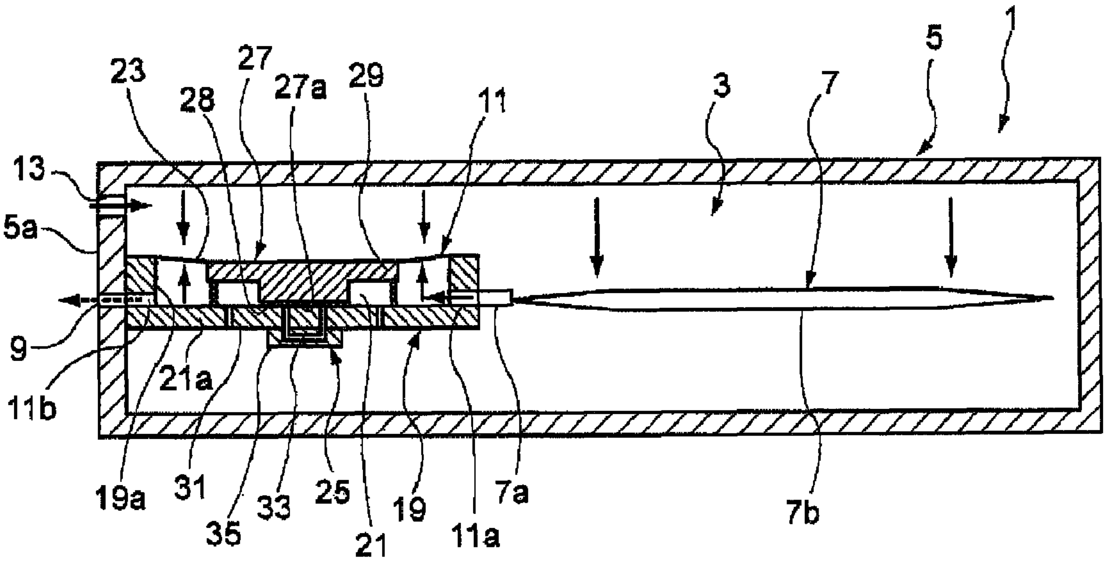
FIG. 3 is a longitudinal cross-sectional view showing a state where a liquid in a liquid containing chamber is exhausted and a pressure space is pressurized in the first embodiment.

FIG. 1 is a longitudinal cross-sectional view showing a liquid container according to a first embodiment of the invention in a state where a liquid remains in a liquid containing chamber and a pressure space is not pressurized. FIG. 2 is a longitudinal cross-sectional view showing a state where a liquid remains in a liquid containing chamber and a pressure space is pressurized. FIG. 3 is a longitudinal cross-sectional view showing a state where a liquid in a liquid containing chamber is exhausted and a pressure space is pressurized.

A liquid container 1 is an ink cartridge that is detachably mounted on a cartridge of an ink jet recording apparatus and supplies ink to a recording head (liquid ejection head) provided in the recording apparatus.

The liquid container 1 includes a container main body 5 that partitions a pressure space (herein after referred to as an airtight space 3) to be pressurized by a pressure unit (not shown), a liquid containing chamber 7 that stores ink, is accommodated in the airtight space 3, and discharges ink stored therein from a discharge port 7*a* by pressure of the airtight space 3, a liquid supply port 9 that is formed to pass through a partition wall 5*a* at one end of the container main body 5 so as to supply ink to a recording head as an external ink liquid consuming apparatus, and a liquid detection portion 11 that is interposed between the liquid containing chamber 7 and the liquid supply port 9 in the airtight space 3 for detecting an ink residual quantity. Here, the airtight space 3 is not limited to a space completely sealed in the airtight manner and the airtight space 3 may be a space to which pressurized air can be introduced as long as serving its function.

The container main body 5 is a boxlike casing and has a pressure port 13 formed at the partition wall 5*a* at one end in a 6-faced partition wall forming the airtight space 3, in addition to the liquid supply port 9. The pressure port 13 is a path through which the pressure unit (not shown) supplies pressurized air to the airtight space 3.

The liquid containing chamber 7 is a so-called ink pack that has a pouch body 7*b* formed by adhering edges of aluminum-laminated multilayer films, in which an aluminum layer is laminated on a resin film layer, to each other. A cylindrical discharge port 7*a*, to which a liquid inlet port 11*a* of the liquid detection portion 11 is connected, is bonded to one end of the pouch body 7*b*. Since the aluminum-laminated multilayer films are used, a high gas barrier property is secured.

The liquid containing chamber 7 and the liquid detection portion 11 are connected to each other by engaging the liquid inlet port 11*a* with the discharge port 7*a*. That is, the liquid containing chamber 7 and the liquid detection portion 11 can be detached from each other by releasing the engagement of the discharge port 7*a* and the liquid inlet port 11*a*.

Ink is filled into the liquid containing chamber 7 in advance at a high degree of deaeration before the liquid detection portion 11 is connected.

The liquid detection portion 11 includes a detection device case 19 that has a recess space 19*a* communicating the liquid inlet port 11*a* connected to the discharge port 7*a* of the liquid containing chamber 7 with a liquid outlet port 11*b* connected to the liquid supply port 9, a diaphragm 23 that functions as a partition wall to seal an opening at an upper surface of the recess space 19*a* so as to partition a liquid detection chamber (liquid storage portion) 21, a vibration detection unit 25 that is provided at the bottom of the recess space 19*a*, a pressure receiving plate 27 that is fixed to an inner surface of the diaphragm 23 to face the vibration detection unit 25 by an adhesive or the like and functions as a plate-shaped rigid wall opposed to a flat surface at a front end of the vibration detection unit 25, and a pressure adjusting spring 29 that is compressed between the pressure receiving plate 27 and the bottom of the recess space 19*a* and functions as an urging unit to urge the pressure receiving plate 27 and the diaphragm 23 in a direction in which the volume of the liquid detection chamber 21 increases.

The pressure adjusting spring 29 urges the diaphragm such that the diaphragm 23 is displaced according to the pressure of ink in the liquid detection chamber 21.

In the detection device case 19, the liquid inlet port 11*a* is integrally formed at one end of a peripheral wall partitioning the recess space 19*a*, and the liquid outlet port 11*b* that communicates with the liquid supply port 9 is formed to pass through a peripheral wall facing the liquid inlet port 11*a*.

Though not shown, a valve mechanism is provided in the liquid supply port 9. The valve mechanism opens a flow passage when the ink cartridge is mounted on a cartridge mounting portion of the ink jet recording apparatus and an ink supply needle provided in the cartridge mounting portion is inserted into the liquid supply port 9.

The diaphragm 23 is formed of a flexible film and applies displacement to the pressure receiving plate 27 according to the pressure of ink to be supplied to the liquid detection chamber 21. In order to enable a little change in pressure of ink to be detected and to improve detection accuracy, what is necessary is that the diaphragm 23 has enough flexibility. Further, in order to prevent a degree of deaeration of ink passing through the liquid detection chamber 21 from being lowered, what is necessary is that an aluminum-laminated multilayer film having an excellent gas barrier property is used as the flexible film constituting the diaphragm 23, similarly to the pouch body 7*b*.

As shown in FIG. 3, the vibration detection unit 25 of the liquid detection portion 11 includes a flat plate-shaped rigid wall 31 that comes into close contact with the pressure receiving plate 27 through a space forming portion 28 when ink of the liquid containing chamber 7 is exhausted and the pressure receiving plate 27 is pressed down against the pressure adjusting spring 29 by a pressure of the pressurized fluid to be supplied from the pressure port 13 into the airtight space 3, an ink guide path 33 that is a concave portion for detection formed at the rigid wall 31, and a piezoelectric detection unit 35 that applies vibration to the ink guide path 33 and detects a change in residual vibration waveform according to the applied vibration. Accordingly, presence/absence of ink (ink residual quantity) is detected from the change in the residual vibration waveform (change in amplitude or frequency) that changes according to the movement of the pressure receiving plate 27 due to the decrease in volume of the liquid detection chamber 21 and whether or not bubbles are mixed. The detection unit of the invention is not limited to a detection unit for detecting a change in residual vibration waveform.

In this embodiment, the rigid wall 31 of the liquid detection chamber 11 constitutes apart of an inner wall (herein after referred to a bottom wall) 21*a* of the liquid detection chamber 21.

The rigid wall 31 of the liquid detection portion 11 and the diaphragm 23 are a pair of opposing walls of the liquid detection chamber 21, a distance therebetween changes according to the change in volume of the liquid detection chamber 21. In this embodiment, it can be seen that the liquid detection portion 11 includes the piezoelectric detection unit 35 at the rigid wall 31 that is one of the pair of opposing walls.

Further, in this embodiment, a space forming portion 28 is provided to space the rigid wall 31 and the pressure receiving plate 27 on the flexible film 23 at a predetermined space when ink in the liquid containing chamber 7 is exhausted and the volume of the liquid detection chamber 21 is minimized, as shown in FIG. 3.

In this embodiment, the space forming portion 28 is a protrusion that protrudes from the surface of the pressure receiving plate 27 facing the piezoelectric detection unit 35.

An urging direction of the pressure adjusting spring 29 is a direction in which the volume of the liquid detection chamber 21 increases, as described above, and a direction opposite to a direction in which the piezoelectric detection unit 35 is disposed.

An urging force F of the pressure adjusting spring 29 to the pressure receiving plate 27 is set such that, when a pressure force by the pressurized fluid to be supplied to the airtight space 3 is P and an internal pressure of the liquid detection chamber 21 by the pressure of ink flowing from the liquid containing chamber 7 into the liquid detection chamber 21 to be then filled therein by the pressure of the pressurized fluid is p1, the relationship P=F+p1 is established.

If an ink containing amount in the liquid containing chamber 7 decreases, when a predetermined pressure operation by the pressurized fluid is performed, the amount of ink flowing from the liquid containing chamber 7 into the liquid detection chamber 21 decreases. Accordingly, the actual internal pressure by the pressure of ink in the liquid detection chamber 21 becomes p2 that is smaller than the prescribed internal pressure p1.

That is, when the airtight space 3 is not pressurized by the pressurized fluid and enough ink remains in the liquid containing chamber 7, the liquid detection chamber 21 is expanded to have the maximum volume by the urging force of the pressure adjusting spring 29.

Thereafter, if the ink containing amount in the liquid containing chamber 7 decreases and the amount of ink flowing from the liquid containing chamber 7 into the liquid detection chamber 21 upon the pressure operation decreases accordingly, a total urging force (F+p2) to be applied to the pressure receiving plate 27 in the liquid detection chamber 21 becomes smaller than the pressure force P by the pressurized fluid according to the relationship (F+p2)<(F+p1)=P. Accordingly, the pressure receiving plate 27 moves in a direction in which the volume of the liquid detection chamber 21 decreases.

FIG. 2 shows a state where, with the supply of pressurized air to the airtight space 3, the liquid containing chamber 7 and the liquid detection portion 11 are pressurized, and an ink liquid in the liquid containing chamber 7 is supplied to the liquid supply port 9 through the liquid detection chamber 21.

If ink of the liquid containing chamber 7 is exhausted and, even if the airtight space 3 is pressurized by pressurized air, ink is not supplied from the liquid containing chamber 7 to the liquid detection chamber 21, an urging force in the liquid detection chamber 21 to the pressure receiving plate 27 is only the urging force of the pressure adjusting spring 29. Then, the pressure receiving plate 27 is pressed against the bottom of the recess space 19*a*, that is, the vibration detection unit 25, by an external pressure of pressurized air. A lower surface 27*a* of the pressure receiving plate 27 is opposed to the surface of the rigid wall 31 (that is, parallel to the horizontal surface). The space forming portion 28 that protrudes from the lower surface 27*a* of the pressure receiving plate 27 comes into contact with the surface of the rigid wall 31, and thus the ink guide path 33 is kept to communicate with the liquid detection chamber 21 through a fine gap (space).

In this embodiment, a time at which the space forming portion 28 of the pressure receiving plate 27 comes into contact with the rigid wall 31 by the decrease in the ink containing amount of the liquid detection chamber 21 and the ink guide path 33 communicates with the liquid detection chamber 21 through the regulated fine gap is set to a state where the liquid in the liquid containing chamber 7 is exhausted.

In the above-described liquid container 1, if the liquid containing amount in the liquid detection chamber 21 is equal to or less than a regular amount, the pressure receiving plate 27 comes into contact with the rigid wall 31 having the ink guide path 33 as the concave portion for detection through the space forming portion 28, and the liquid detection chamber 21 that communicates with the ink guide path 33 as a vibration reaction region becomes a limited narrow space. Accordingly, a change in the residual vibration waveform markedly appears, and thus a time or a state where the liquid residual quantity in the liquid containing chamber 7 or the liquid detection chamber 21 reaches a predetermined level can be accurately and reliably detected.

The liquid detection chamber 21 is separated from the liquid containing chamber 7. Accordingly, when the liquid containing chamber 7 contains the liquid in the flexible pouch body 7*b*, even if bending or wrinkle occurs in the flexible pouch body 7*b* due to the decrease in the ink residual quantity of the liquid containing chamber 7, bending or wrinkle of the pouch body 7*b* does not affect detection accuracy of the piezoelectric detection unit 35.

Even if ink in the liquid containing chamber 7 is exhausted and the volume of the liquid detection chamber is minimized, a predetermined space is secured between the detection unit 35 and the pressure receiving plate 27 as the opposing wall in the liquid detection chamber 21. Accordingly, if the detection unit 35 is normally operating, the residual vibration waveform corresponding to the amount of ink remaining in the space can be detected. Therefore, there rarely occurs that a case where the change in residual vibration waveform cannot be detected due to a failure of the detection unit 35 and a case where the liquid is exhausted are erroneously judged. As a result, it is possible to accurately detect that the liquid is exhausted.

Accordingly, it is possible to stably detect the ink residual quantity with high accuracy while preventing bending or wrinkle of the flexible pouch body 7*b* containing the liquid from affecting detection accuracy of the ink residual quantity.

In this embodiment, when the space forming portion 28 is the protrusion that protrudes from the surface of the pressure receiving plate 27 facing the detection unit 35 of the liquid detection chamber 21 and the pressure receiving plate 27 is a molded product formed of resin, the protrusion can be integrally formed, such that the number of parts is not increased. That is, manufacturing costs can be prevented from being increased due to the increase in the number of parts.

In the liquid detection portion 11 of this embodiment having the diaphragm 23 and the rigid wall 31 as the pair of opposing walls that change the distance therebetween due to the change in volume, the piezoelectric detection unit 35 is provided at the rigid wall 31, and the plate-shaped pressure receiving plate 27 is provided at the diaphragm 23 to be opposed to a flat surface at a front end of the detection unit 35. The protrusion serving as the space forming portion 28 is provided at the pressure receiving plate 27. Further, the pressure adjusting spring 29 is provided in the liquid detection chamber 21 to urge the diaphragm 23 such that the diaphragm 23 is displaced according to the pressure of the liquid in the liquid detection chamber 21. In addition, the detection unit 35 is disposed in the liquid detection chamber 21 that is separated from the liquid containing chamber 7. In such a manner, the liquid detection portion 11 that uses the change in residual vibration waveform for detecting the ink residual quantity can be relatively simply constructed.

In this embodiment, the diaphragm 23 is formed of a flexible film. Accordingly, if the aluminum-laminated multilayer film, in which the aluminum layer is laminated on the resin film layer, is used as the flexible film, a high gas barrier property can be secured in the liquid detection chamber 21. Further, since a degree of deaeration of ink contained in the liquid containing chamber 7 is not lowered due to the gas barrier property in the liquid detection chamber 21, ink at a high degree of deaeration can be supplied to the ink jet recording apparatus as the liquid consuming apparatus.

If the liquid container 1 of this embodiment is used as an ink container that supplies ink to the ink jet recording apparatus, the ink residual quantity can be accurately detected. Accordingly, a trouble can be prevented from occurring due to degradation of the detection accuracy or erroneous detection of the ink residual quantity. Therefore, operation reliability in the ink jet recording apparatus can be improved.

In the liquid detection portion 11 of this embodiment, the liquid detection chamber 21 is initially set to the maximum internal volume, and then the internal volume of the liquid detection chamber 21 gradually decreases as ink in the liquid containing chamber 7 is consumed. Then, if ink in the liquid containing chamber 7 is exhausted, the internal volume of the liquid detection chamber 21 is minimized. Accordingly, the diaphragm 23 that supports the pressure receiving plate 27 of the liquid detection chamber 21 is gradually deformed in a direction in which the internal volume of the liquid detection chamber 21 gradually decreases.

That is, the occurrence of large deformation on the basis of a change in internal volume of the liquid detection chamber 21 from the maximum to the minimum is just one time until the liquid in the liquid containing chamber 7 is exhausted. Accordingly, the diaphragm 23 as a flexible wall of the liquid detection chamber 21 does not frequently repeat the large deformation, unlike the structure in which the liquid detection portion is provided outside the airtight space 3. Therefore, a cheap material having lower durability can be used for the diaphragm 23 as the flexible wall of the liquid detection chamber 21. As a result, the liquid detection portion 11 can be implemented at low cost.

In the liquid detection portion 11 of the liquid container 1 of this embodiment, the diaphragm 23 is bonded to the detection device case 19, in which the recess space 19*a* having an opened upper surface is formed, so as to seal the opening of the upper surface of the recess space 19*a*, thereby partitioning the liquid detection chamber 21. Further, since the diaphragm 23 that seals the opening of the recess space 19*a* serves as a flexible wall that enables the change in volume of the liquid detection chamber 21, the liquid detection chamber 21 having a volume change characteristic (compliance) can be simply formed at low cost.

In the liquid detection portion 11 of the liquid container 1 of this embodiment, as the urging unit that urges the pressure receiving plate 27 in a direction distant from the piezoelectric detection unit 35, the pressure adjusting spring 29 formed of an elastic member is used.

Accordingly, the urging force of the pressure adjusting spring 29 can be simply increased or decreased by changing quality of the elastic member or the like. Then, by increasing or decreasing the urging force, a time at which the pressure receiving plate 27 closes the ink guide path 33 that is the concave portion for detection can be changed. Accordingly, the liquid residual quantity to be detected in the liquid detection chamber 21 can be easily set and changed.

In the liquid detection portion 11 of the liquid container 1 of this embodiment, a time at which the space forming portion 28 of the pressure receiving plate 27 comes into contact with the rigid wall 31 is set to a state where the liquid of the liquid containing chamber 7 is exhausted. Accordingly, for example, when the liquid container 1 is used as an ink cartridge, the piezoelectric detection unit 35 of the liquid detection portion 11 can be efficiently used as an ink end detection mechanism for detecting that the ink residual quantity in the liquid containing chamber 7 becomes zero.

Moreover, a time at which the pressure receiving plate 27 forms the ink guide path 33 in the airtight space in cooperation with the rigid wall 31 may be set to a state where the liquid of the liquid containing chamber 7 is nearly exhausted.

If doing so, for example, when the liquid container 1 is used as an ink cartridge, the piezoelectric detection unit 35 of the liquid detection portion 11 can be efficiently used an ink end detection unit for detecting a state where the ink residual quantity in the liquid containing chamber 7 almost becomes zero.

In the above-described embodiment, the pressure receiving plate 27 is fixed to the inner surface of the diaphragm 23 by an adhesive or the like. However, the pressure receiving plate 27 may not be fixed to the diaphragm 23. For example, the pressure receiving plate 27 may be kept to come into contact with the diaphragm 23 by the urging force of the pressure adjusting spring 29 that urges the pressure receiving plate 27 in a direction distant from the rigid wall 31.

In the first embodiment, the protrusion serving as the space forming portion 28 is provided at the pressure receiving plate 27, however the invention is not limited to this embodiment. A second embodiment will be described below with reference to FIGS. 4 and 5.

Figure 4:
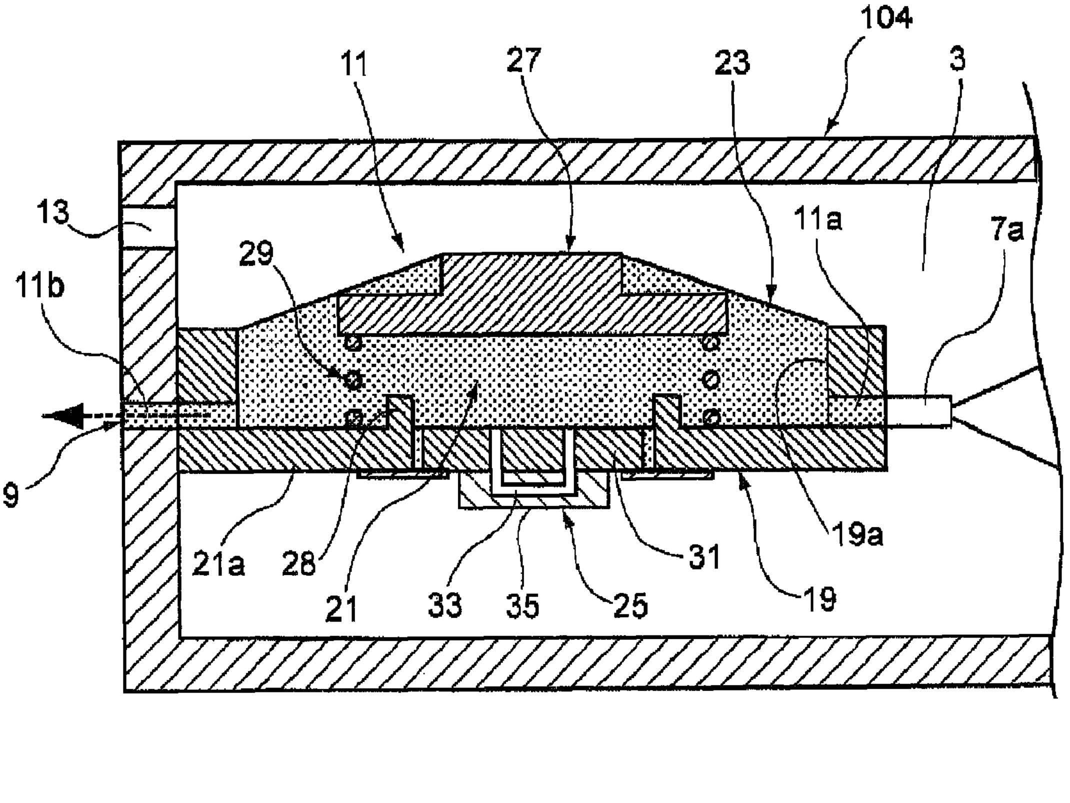
FIG. 4 is a longitudinal cross-sectional view showing a liquid container according to a second embodiment of the invention in a state where a liquid remains in a liquid containing chamber and a pressure space is not pressurized.
Figure 5:
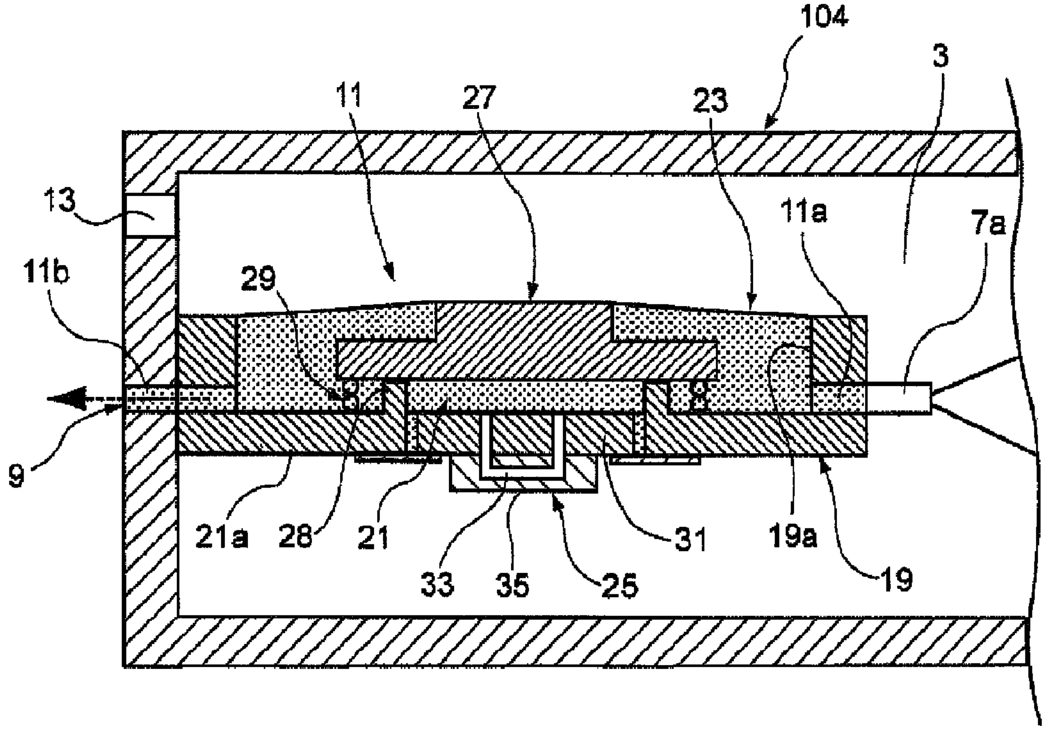
FIG. 5 is a longitudinal cross-sectional view showing a state where a liquid in a liquid containing chamber is exhausted and a pressure space is pressurized in the second embodiment.

FIG. 4 is a longitudinal cross-sectional view showing a liquid container according to the second embodiment of the invention in a state where a liquid remains in the liquid containing chamber and the pressure space is not pressurized. FIG. 5 is a longitudinal cross-sectional view showing a state in the second embodiment where a liquid in the liquid containing chamber is exhausted and the pressure space is pressurized.

In the liquid container 104 shown in FIG. 4, the space forming portion 28 is provided at the bottom wall 21*a*. The space forming unit 28 formed at the bottom wall 21*a* is a protrusion protruding from the bottom wall 21*a* toward the pressure receiving plate 27. The protrusion serving as the space forming portion 28 may be formed with the recess space 19*a* as one piece or formed as different pieces after the recess space 19*a* is formed.

In this embodiment, the bottom wall 21*a* of the liquid detection chamber 21 and the diaphragm 23 are a pair of opposing walls of the liquid detection chamber 21, which change a distance therebetween according to the change in volume of the liquid detection chamber 21. In the liquid detection portion 11 of this embodiment, the piezoelectric detection unit 35 is provided at the rigid wall 31 forming a part of the bottom wall 21*a* that is one of the pair of opposing walls.

Further, in this embodiment, the protrusion serving as the space forming portion 28 is provided so as to protrude from the bottom wall 21*a* of the liquid detection chamber 21 for securing a space between the bottom wall 21*a* and the diaphragm 23 that is a pair of opposing walls when ink in the liquid containing chamber 7 is exhausted and the volume of the liquid detection chamber 21 is minimized as shown in FIG. 5.

In the second embodiment described above, similarly to the first embodiment, the object of the invention can be achieved.

Figure 6:
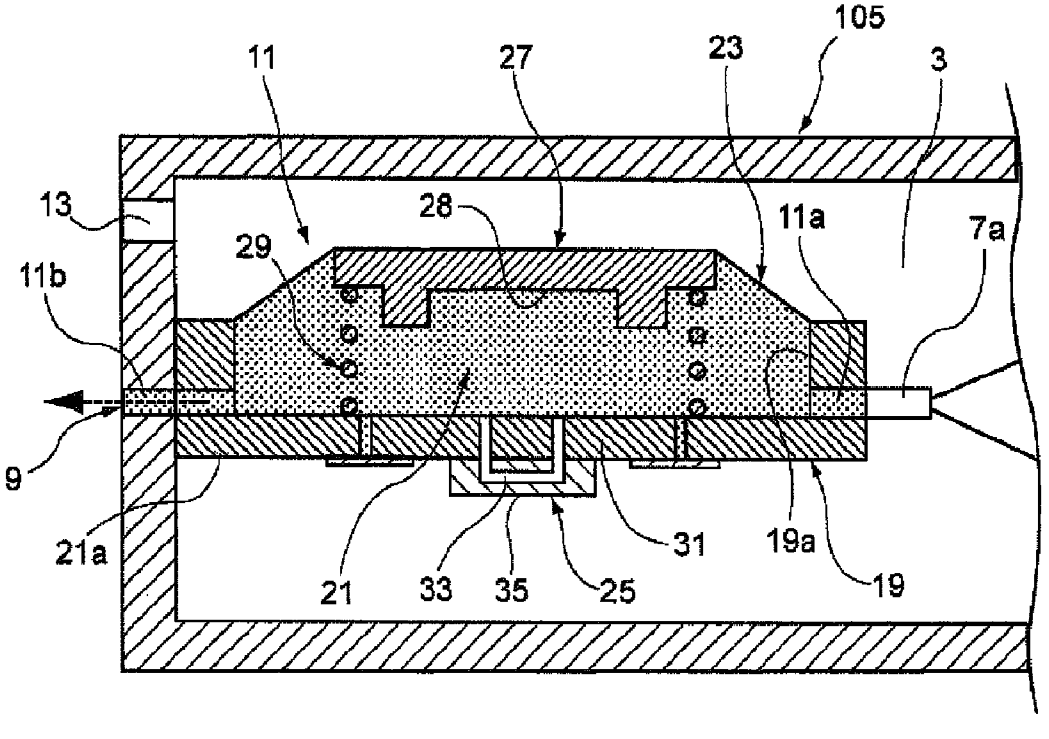
FIG. 6 is a longitudinal cross-sectional view showing a liquid container according to a third embodiment of the invention in a state where a liquid remains in a liquid containing chamber and a pressure space is not pressurized.
Figure 7:
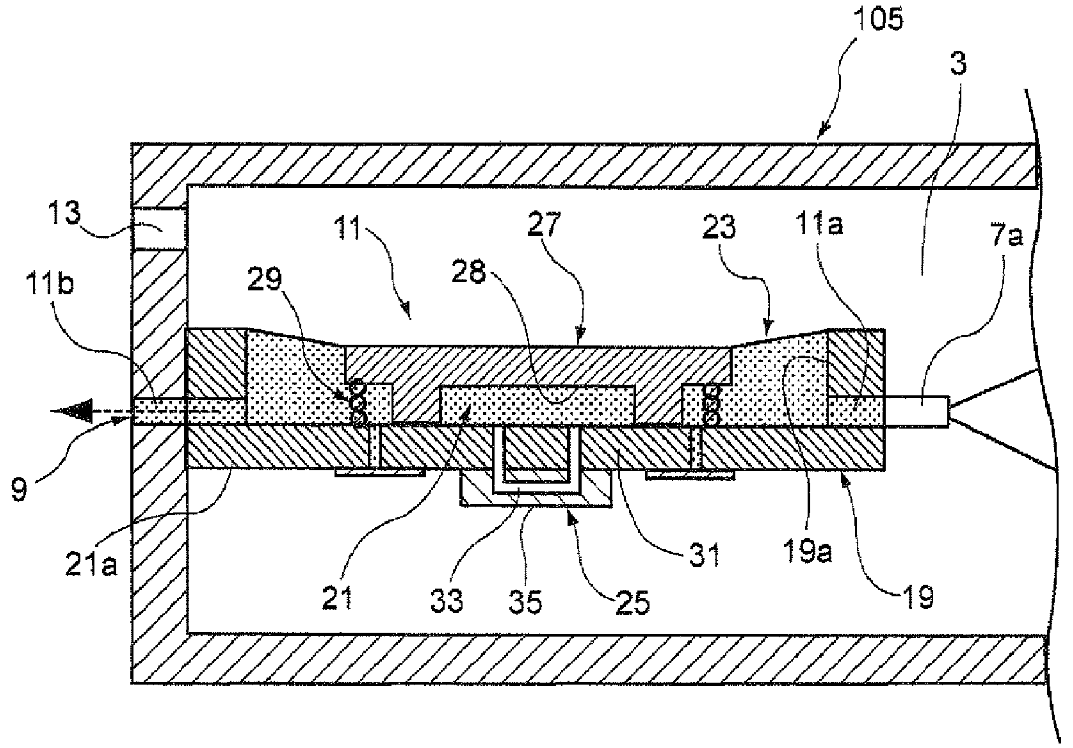
FIG. 7 is a longitudinal cross-sectional view showing a state where a liquid in a liquid containing chamber is exhausted and a pressure space is pressurized in the third embodiment.

Next, a third embodiment will be described below with reference to FIGS. 6 and 7. FIG. 6 is a longitudinal cross-sectional view showing a liquid container according to the third embodiment of the invention in a state where a liquid remains in the liquid containing chamber and the pressure space is not pressurized. FIG. 7 is a longitudinal cross-sectional view showing a state in the third embodiment where a liquid in the liquid containing chamber is exhausted and the pressure space is pressurized.

The space forming portion 28 in this embodiment is different from that in the first embodiment. Although the space forming portion 28 in the liquid container 1 of the first embodiment is the protrusion formed at the pressure receiving plate 27, the space forming portion 28 in this embodiment is a recess provided at the pressure receiving plate 27 in a position opposing the ink guide path 33 of the vibration detection unit 25.

Further, in this embodiment, a space is secured by the recess defined between the rigid wall 31 and the diaphragm 23 that is a pair of opposing walls when ink in the liquid containing chamber 7 is exhausted and the volume of the liquid detection chamber 21 is minimized as shown in FIG. 7.

With this configuration, in the third embodiment described above, similarly to the first embodiment, the object of the invention can be achieved.

Moreover, in the liquid detection portion according to the invention, the position where the vibration detection unit 25 is provided or the position where the space forming portion 28 is not limited to the above-described embodiment.

Figure 8:
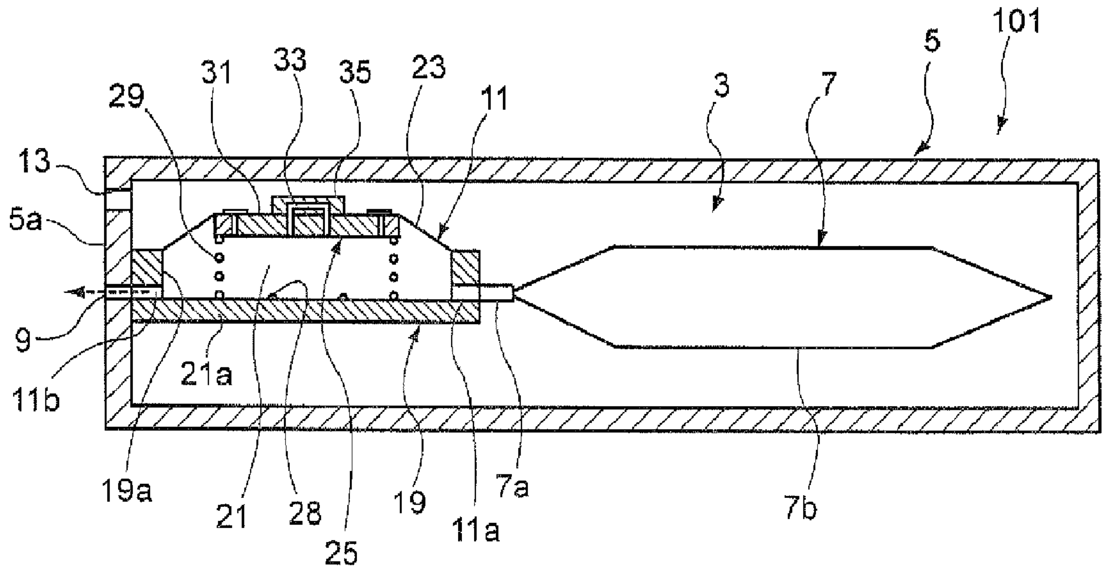
FIG. 8 is a longitudinal cross-sectional view showing a liquid container according to a fourth embodiment of the invention in a state where a liquid remains in a liquid containing chamber and a pressure space is not pressurized.

For example, the vibration detection unit 25 and the space forming portion 28 may be disposed as shown in FIG. 8.

A liquid container 10 shown in FIG. 8 is a liquid container according to a fourth embodiment of the invention. A vibration detection unit 25 having a piezoelectric detection unit 35 is provided at a diaphragm 23 that is one of a pair of opposing walls of a liquid detection chamber 21 that changes a distance therebetween according to a change in volume of the liquid detection chamber 21. Further, a bottom wall 21*a* of the liquid detection chamber facing the diaphragm 23 functions as the other opposing wall. A space forming portion 28 is provided at the bottom wall of the detection device case 19 as a protrusion.

That is, in the liquid container 101 of the fourth embodiment having the pair of opposing walls of the liquid detection chamber 21 that changes the distance therebetween according to the change in volume of the liquid detection chamber 21, one wall is formed by the diaphragm 23 that is displaced according to a change in pressure, and the other wall is formed by the bottom wall 21*a* of the liquid detection chamber 21. The detection unit 35 is provided at the rigid wall 31 affixed to the diaphragm 23. The space forming portion 28 is provided at the bottom wall 21*a* of the liquid detection chamber 21 facing a flat surface at a front end of the detection unit 35 for forming a predetermined space between the vibration detection unit 25 and the bottom wall 21*a*. Moreover, the specific configuration of the vibration detection unit 25 and the configuration of the pressure adjusting spring 29 that is provided in the liquid detection chamber 21 to urge the diaphragm 23 are the same as those in the first embodiment.

With the configuration of the fourth embodiment, similarly to the first embodiment, the detection unit 35 is disposed in the liquid detection chamber 21 that is separated from the liquid containing chamber 7. Accordingly, the liquid detection portion 11 that uses the change in residual vibration waveform for detecting the ink residual quantity can be relatively simply constructed.

Further, since the pressure receiving plate 27 as a separate part is not required, the number of parts is reduced, and thus costs can be reduced.

Figure 9:
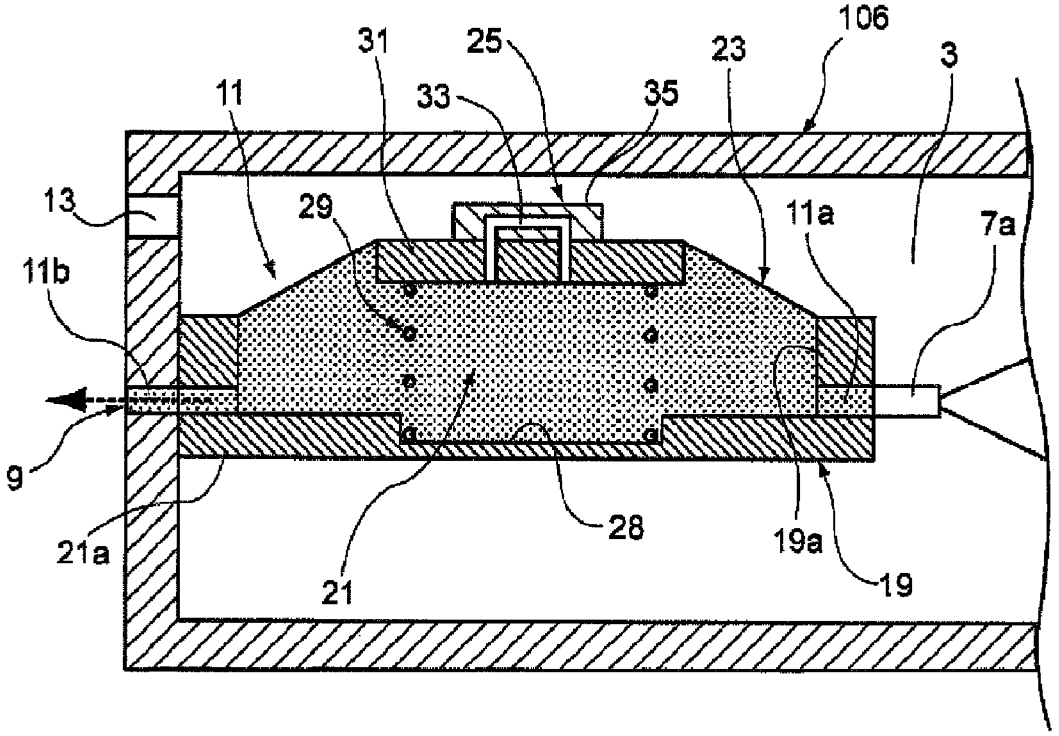
FIG. 9 is a longitudinal cross-sectional view showing a liquid container according to a fifth embodiment of the invention in a state where a liquid remains in a liquid containing chamber and a pressure space is not pressurized.
Figure 10:
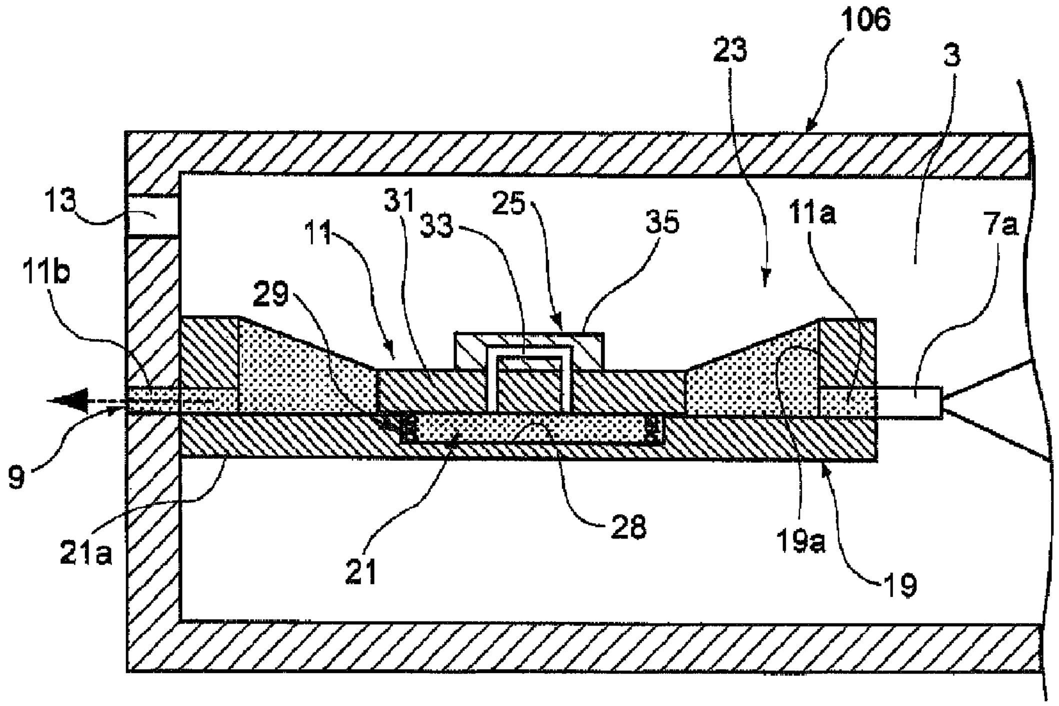
FIG. 10 is a longitudinal cross-sectional view showing a state where a liquid in a liquid containing chamber is exhausted and a pressure space is pressurized in the fifth embodiment.

Next, a fifth embodiment will be described below with reference to FIGS. 9 and 10. FIG. 9 is a longitudinal cross-sectional view showing a liquid container according to the fifth embodiment of the invention in a state where a liquid remains in the liquid containing chamber and the pressure space is not pressurized. FIG. 10 is a longitudinal cross-sectional view showing a state in the fifth embodiment where a liquid in the liquid containing chamber is exhausted and the pressure space is pressurized.

The space forming portion 28 in this embodiment is different from that in the fourth embodiment. Although the space forming portion 28 in the liquid container 101 of the fourth embodiment is the protrusion formed at the bottom wall 21*a* of the liquid detection chamber 21, the space forming portion 28 in a liquid container 106 shown in FIG. 9 of this embodiment is a recess provided at the bottom wall 21*a* of the liquid detection chamber 21 in a position opposing the ink guide path 33 of the vibration detection unit 25.

Further, in this embodiment, a space is secured by the recess as the space forming portion 28 defined between the bottom wall 21*a* of the liquid detection chamber 21 and the rigid wall 31 affixed to the diaphragm 23 that is a pair of opposing walls when ink in the liquid containing chamber 7 is exhausted and the volume of the liquid detection chamber 21 is minimized as shown in FIG. 10.

With this configuration, in the fifth embodiment described above, similarly to the fourth embodiment, the object of the invention can be achieved.

Moreover, in the liquid container according to the invention, the position where the liquid detection portion 11 is provided is not limited to the inside of the airtight space 3, in which the liquid containing chamber 7 is accommodated.

Like a sixth or seventh embodiment described below, the liquid detection portion 11 can be disposed in an external exclusive-use accommodating space separated from the airtight space 3, in which the liquid containing chamber 7 is accommodated.

Figure 11:
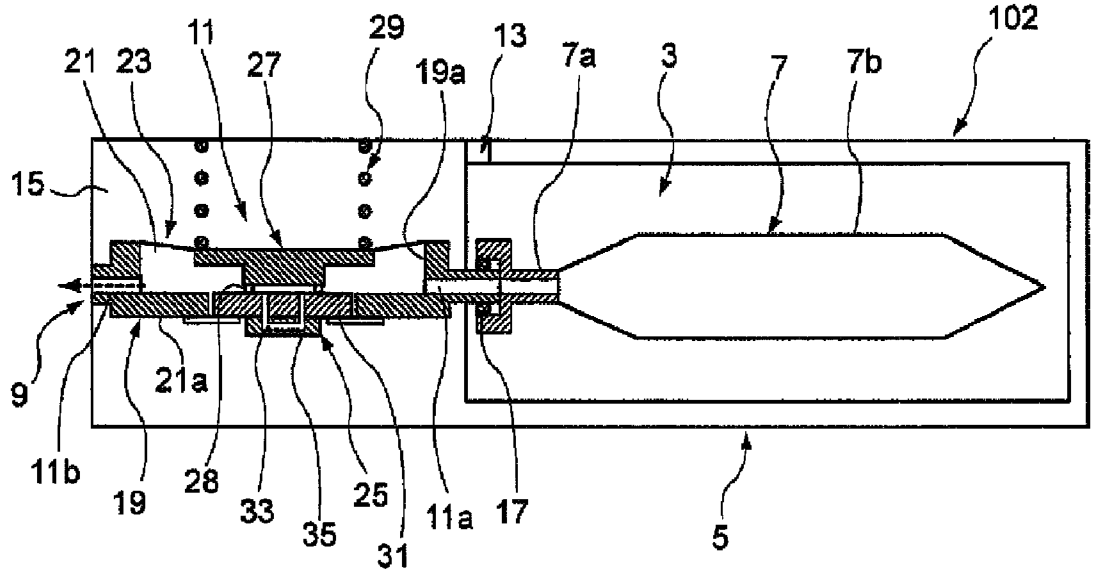
FIG. 11 is a longitudinal cross-sectional view showing a liquid container according to a sixth embodiment of the invention in a state where a liquid remains in a liquid containing chamber and a pressure space, in which a liquid containing chamber is provided, is not pressurized.
Figure 12:
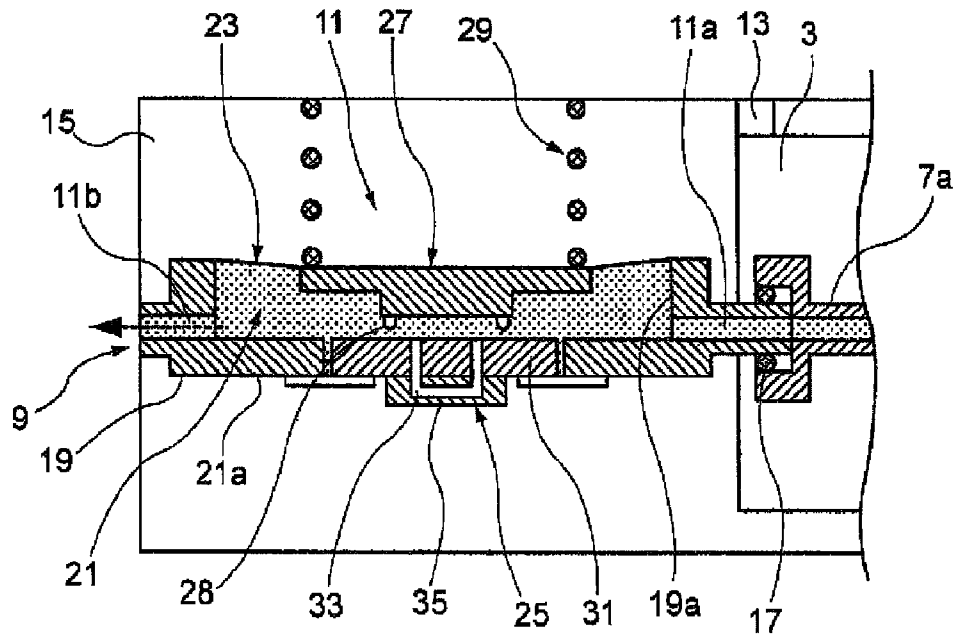
FIG. 12 is an enlarged cross-sectional view of a liquid container shown in FIG. 11, which shows a state where a liquid is absorbed from a non-pressurized liquid containing chamber through a liquid supply port.

FIG. 11 is a longitudinal cross-sectional view showing a liquid container according to a sixth embodiment of the invention in a state where a liquid remains in a liquid containing chamber and an airtight space, in which a liquid containing chamber is provided, is not pressurized. FIG. 12 is an enlarged cross-sectional view of a liquid container shown in FIG. 11, which shows a state where a liquid is absorbed from a non-pressurized liquid containing chamber through a liquid supply port.

In a liquid container 102 of the sixth embodiment, the liquid detection portion 11 in the liquid container 1 of the first embodiment is moved to a separately partitioned detection unit accommodating chamber 15 outside the airtight space 3, in which the liquid containing chamber 7 is accommodated.

Further, as the liquid detection portion 11 is changed to a detection unit accommodating chamber 15 outside the airtight space 3, the arrangement of the pressure adjusting spring 29 that urges the diaphragm 23 of the liquid detection chamber 21 is changed. The pressure adjusting spring 29 that is mounted in a compressed state between the diaphragm 23, to which the pressure receiving plate 27 is fixed, and the inner wall of the detection unit accommodating chamber 15. The pressure adjusting spring 29 urges the diaphragm 23 toward the bottom portion of the detection device case 19 (in a direction in which the volume of the liquid detection chamber 21 decreases).

Although the arrangement of the pressure adjusting spring 29 is changed, other parts are the same as those in the liquid container 1 of the first embodiment. The same parts are represented by the same reference numerals, and the descriptions thereof will be omitted.

Figure 13:
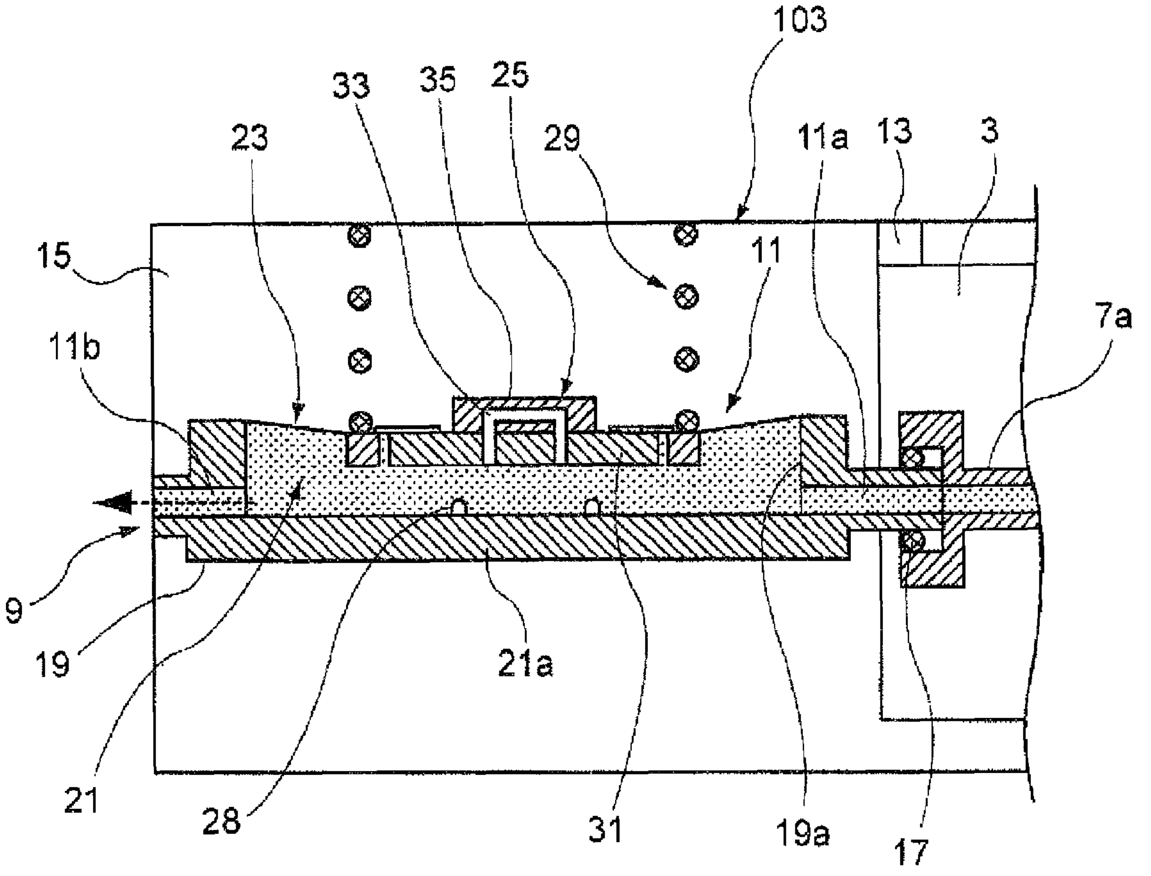
FIG. 13 is an enlarged cross-sectional view of a liquid detection portion connected to a liquid containing chamber in a liquid container according to a seventh embodiment of the invention.

FIG. 13 is an enlarged cross-sectional view of a liquid detection portion connected to the liquid containing chamber in the liquid container according to a seventh embodiment of the invention.

In a liquid container 103 according to the seventh embodiment, the liquid detection portion 11 in the liquid container 101 of the fourth embodiment is moved to the detection unit accommodating chamber 15 separately partitioned outside the airtight space 3, in which the liquid containing chamber 7 is accommodated.

Similarly to the fifth embodiment, as the liquid detection portion 11 is changed to the detection unit accommodating chamber 15 outside the airtight space 3, the arrangement of the pressure adjusting spring 29 that urges the diaphragm 23 of the liquid detection chamber 21 is changed. That is, the pressure adjusting spring 29 is mounted in a compressed state between the diaphragm 23, to which the rigid wall 31 of the vibration detection unit 25 is fixed, and the detection unit accommodating chamber 15. The pressure adjusting spring 29 urges the diaphragm 23 toward the bottom portion of the detection device case 19 (in a direction in which the volume of the liquid detection chamber 21 decreases).

Although the arrangement of the pressure adjusting spring 29 is changed, other parts are the same as those in the liquid container 101 of the fourth embodiment. The same parts are represented by the same reference numerals, and the descriptions thereof will be omitted.

In the sixth or seventh embodiment described above, similarly to the first or second embodiment, the object of the invention can be achieved.

That is, the liquid detection portion 11 views the change in volume of the liquid detection chamber 21 due to the decrease in the ink residual quantity of the liquid containing chamber 7 as the change in vibration waveform, and uses the vibration waveform for detecting the ink in the liquid containing chamber 7. Further, the liquid detection chamber 21 is separated from the liquid containing chamber 7. Accordingly, when the liquid containing chamber 7 contains the liquid in the flexible pouch body, even if bending or wrinkle occurs in the flexible pouch body **7*b* due to the decrease in the ink residual quantity of the liquid containing chamber 7, bending or wrinkle of the pouch does not affect the detection accuracy of the piezoelectric detection unit 35**.

In addition, even if ink in the liquid containing chamber 7 is exhausted and the volume of the liquid detection chamber is minimized, a predetermined space is secured between the detection unit 35 and the opposing wall in the liquid detection chamber 21 by the space forming portion 28. Accordingly, if the detection unit 35 is normally operating, the residual vibration waveform corresponding to the amount of ink remaining in the space is detected. Therefore, there is no case where the change in the residual vibration waveform cannot be detected due to a failure of the detection unit or the like or it is erroneously detected that ink is exhausted. As a result, it is possible to accurately detect that ink is exhausted.

Accordingly, it is possible to stably detect the ink residual quantity with high accuracy while preventing bending or wrinkle of the flexible pouch body **7*b*** containing ink from affecting the detection accuracy of the ink residual quantity.

The use of the liquid container according to the invention is not limited to the ink cartridge of the ink jet recording apparatus.

The invention can be applied to various types of a liquid consuming apparatus having a liquid ejection head. For example, the invention may be concretized to a printer of a full line type in which a recording head has an entire shape corresponding to a length of a widthwise direction (horizontal direction) of a recording sheet (not shown) in a direction perpendicular to a transport direction (anteroposterior direction) of the recording sheet. In addition, in the above embodiments, a liquid consuming apparatus is concretized to an ink jet printer, however it is not limited to the ink jet printer. It may be concretized to a fluid ejection apparatus splashing or ejecting liquid state material (fluid state material such as gel may be included), that is other than ink, in which particles of function material are dispersed or mixed. For example, It may be a liquid ejection apparatus ejecting a liquid state material in which an electrode material or color material (pixel material) is dispersed or dissolved and which is used in manufacturing a liquid crystal display, an organic light emission display (electro luminescence) or surface emission display or the like, a liquid ejection apparatus ejecting a bioorganic material used in manufacturing a bio-chip, or a liquid ejection apparatus ejecting a liquid that is a sample as a precision pipette. Further, it may be a liquid ejection apparatus pinpoint ejecting lubricant to a precision instrument such as a watch or camera or the like, a liquid ejection apparatus ejecting on a substrate a transparent resin liquid such as ultraviolet cure resin for forming a fine hemispheric lens (optical lens) for use in an optical communication element or the like, a liquid ejection apparatus ejecting an etching liquid such as acid or alkali for etching a substrate or the like, or a liquid ejection apparatus ejecting a liquid state material such as gel (for example, physical gel). In this specification, the term “liquid” includes an inorganic solvent, an organic solvent, a solution, a liquid resin, a liquid metal (metal melt) or the like, or a liquid state material, a fluid state material or the like.

The entire disclosure of Japanese Patent Application No: 2006-114847, filed on Apr. 18, 2006 is expressly incorporated by reference herein.

While this invention has been described in conjunction with the specific embodiments thereof, it is evident that many alternatives, modifications, and variations will be apparent to those skilled in the art. Accordingly, preferred embodiments of the invention as set forth herein are intended to be illustrative, not limiting. There are changes that may be made without departing from the sprit and scope of the invention.

What is claimed is:

1. A liquid container comprising:

a pressure space;

a liquid containing chamber accommodated in the pressure space and storing liquid therein, the liquid containing chamber configured to be pressurized by a pressurized fluid introduced into the pressure space to discharge the liquid therefrom; and a liquid detection portion including:

a liquid detection chamber having a liquid inlet port communicating with the liquid containing chamber and introducing the liquid into the liquid detection chamber and a liquid outlet port adapted to be communicated with a liquid consuming apparatus, a volume of the liquid detection chamber being variable;

first and second walls opposing each other with the liquid therebetween, a distance between the first and second walls being variable in accordance with the volume of the liquid detection chamber;

a detector attached to an outer surface of one of the first and second walls; and a space forming portion configured to form a space between the first and second walls when parts of the first and second walls come in direct contact with each other, the space comprising a portion of the liquid detection chamber, the liquid detection portion configured to be used to detect an amount of the liquid remaining in the liquid container based on a change in residual vibration wave form corresponding to an amount of the liquid remaining in the space, wherein the detector includes:

a passage, provided internal to the detector, the passage communicating with the liquid provided in the space of the liquid detection chamber, and a piezoelectric element configured to apply vibrations to the passage.

2. The liquid container according to claim 1, wherein the space forming portion is a protrusion that protrudes from one of the first and second walls.

3. The liquid container according to claim 2, wherein;

the first wall includes a diaphragm;

the second wall includes a rigid wall;

the detector is attached to the rigid wall;

the first wall includes a pressure receiving plate opposing the detector;

the protrusion is provided at the pressure receiving plate; and the liquid container further comprises a spring urging the pressure receiving plate.

4. The liquid container according to claim 3, wherein the rigid wall is formed by an inner wall of the liquid detection chamber.

5. The liquid container according to claim 1, wherein the space forming portion is a recess provided at one of the first and second walls.

6. The liquid container according to claim 2, wherein:

the first wall includes a diaphragm;

the detector is attached to the diaphragm; and the liquid container further comprises a spring urging the diaphragm.

7. The liquid container according to claim 5, wherein:

the first wall includes a diaphragm;

the detector is attached to the diaphragm; and the liquid container further comprises a spring urging the diaphragm.

8. The liquid container according to any one of claims 3, 6 and 7, wherein the diaphragm is formed of a flexible film.

9. The liquid container according to claim 1, wherein the liquid is ink.

10. The liquid container according to claim 5, wherein;

the first wall includes a diaphragm;

the second wall includes a rigid wall;

the detector is attached to the rigid wall;

the first wall includes a pressure receiving plate opposing the detector;

the protrusion is provided at the pressure receiving plate; and the liquid container further comprises a spring urging the pressure receiving plate.

11. The liquid container according to claim 10, wherein the rigid wall is formed by an inner wall of the liquid detection chamber.

12. The liquid container according to claim 10, wherein the diaphragm is formed of a flexible film.

* * * * *